(12) United States Patent
Tadman

(10) Patent No.: US 8,114,040 B2
(45) Date of Patent: Feb. 14, 2012

(54) INTERCHANGEABLE RANGE OF MOTION STOP

(76) Inventor: Robert LaVerne Tadman, Wautoma, WI (US)

(*) Notice: Subject to any disclaimer, the term of this patent is extended or adjusted under 35 U.S.C. 154(b) by 328 days.

(21) Appl. No.: 12/399,942

(22) Filed: Mar. 7, 2009

(65) Prior Publication Data

US 2009/0240184 A1    Sep. 24, 2009

Related U.S. Application Data

(60) Provisional application No. 61/034,944, filed on Mar. 7, 2008.

(51) Int. Cl.
*A61F 5/00* (2006.01)

(52) U.S. Cl. .................. 602/20; 602/21; 602/22

(58) Field of Classification Search .......... 602/20–22, 602/26–27; 128/878–879
See application file for complete search history.

(56) References Cited

U.S. PATENT DOCUMENTS 4,602,620 A * 7/1986 Marx ............................ 602/21
4,765,320 A * 8/1988 Lindemann et al. ............ 602/22

* cited by examiner

*Primary Examiner* — Michael A. Brown
(74) *Attorney, Agent, or Firm* — Michael Ries

(57) ABSTRACT

A method and apparatus for providing a range of motion to digits on a person's hand is disclosed. The apparatus may include a splint, an outrigger, a plurality of tubes, and a plurality of rubber bands. The outrigger may be secured to the splint and the plurality of tubes may be connected to the outrigger. The plurality of tubes may be provided in varying lengths such that a variety of range of motion requirements may be accommodated by a single kit.

14 Claims, 4 Drawing Sheets

INTERCHANGEABLE RANGE OF MOTION STOP

CLAIM FOR PRIORITY TO PROVISIONAL APPLICATION

This application claims priority to U.S. Provisional Application No. 61/034,944, filed on 7 Mar. 2008, the entire disclosure of which is incorporated herein by reference.

FIELD OF THE INVENTION

The present invention relates generally to a readily adjustable motion control extremity splinting apparatus for a human extremity that is resistant to slipping and does not require frequent replacement of the basic splint when adjustments are required in order to change the degrees of digit(s) restriction need to be made for physical therapy or for day to day activities, and more specifically relates to a method of easily setting and maintaining a range of motion stop for a splint as determined by a doctor or physical therapist during treatment.

BACKGROUND OF THE INVENTION

In the past, therapists improvised motion stops for extremities, such as the hand, that slipped and caused therapists to re-measure the degrees again and again. This caused frustration and the risk of increased injury to patients. Movements of digits (fingers) on the hands are related to types of motion that may need to be restricted to various degrees during exercise and stretching therapy while healing, depending upon the therapy needed. These two types of motion may be generally described as (i) flexion and extension related to opening and closing the hand and (ii) spreading digits apart or retracting digits from a spread-apart position.

Accordingly, there is a need for apparatus for splinting of extremities that can be readily and easily adjusted to provide particular degrees of restriction with respect to one or more of two types of directions that are described above without the need for completely re-splinting an extremity when a change in the degrees of restriction are needed, and to avoid a need to re-splint when slippage of the splint occurs.

SUMMARY OF THE INVENTION

An object of the present invention is to provide a readily adjustable motion control extremity splinting apparatus that is resistant to slipping and does not require frequent replacement of the basic splint when adjustments are required to change the degrees of digit(s) restriction need to be made for physical therapy or for day to day wearing, wherein the splinting apparatus comprises:

(a) a removable or non-removable basic splinting device or casting that is affixed to the limb above an extremity and may be attached to the extremity to restrict movement, comprising one or more distal attachment points with respect to the limb and one or more proximal attachment points with respect to the limb, wherein the proximal and digital attachment points directly or indirectly provide attachment points for adjustable digital movement restriction apparatus, (b) at least one outrigger wire or tube located above and on the posterior portion of the hand and splint, (c) a plurality of attachment anchoring devices having at least two holes, (d) a plurality of single or paired adjustable length anchoring tubes or rods, (e) a plurality of digital splinting apparatus for individually splinting each digit whose movement is to be restricted, each digital splinting apparatus having at least one attachment point for attaching at least one monofilament that may be a cord, rope, string or wire, wherein the cord, rope or string either attaches to an attachment anchoring device located on the outrigger wire or tube or attached to an end of a single or paired anchoring tube or rod.

A preferred object of the present invention is to a readily adjustable motion control extremity splinting apparatus as described above, wherein the adjustable splinting apparatus comprises:

(a) a removable or non-removable basic splinting device or casting that is affixed to the limb above an extremity and may be attached to the extremity to restrict movement, comprising one or more distal attachment points with respect to the limb and one or more proximal attachment points with respect to the limb, wherein the proximal and digital attachment points directly or indirectly provide attachment points for adjustable digital movement restriction apparatus, (b) an outrigger wire or tube located above and on the posterior portion of the hand and splint wherein the wire or tube is firmly or rotationally attached to one or more distal attachment points of the basic splinting device, as described in (a), and the outrigger wire or tube passes through a hole located in each of a plurality of attachment anchoring devices, (c) a plurality of attachment anchoring devices as described in (b) having at least two perpendicular holes in each anchoring device through which the outrigger tube may be passed and through which a second adjustable length anchoring tube or rod may be passed and may be fixed at a particular length, wherein the attachment anchoring devices may comprise a single unit with at least two perpendicular holes, or may have two portions with matching grooves perpendicular to a single hole wherein the matching groves collectively form a round hole when the two portions are affixed together around the outrigger wire or tube, and optionally comprising a further hole or outlet as an attachment point for a cord, rope, string or wire, (d) a plurality of adjustable length anchoring tubes or rods, wherein a portion of each anchoring tube or rod partially or fully passes through a hole in an individual attachment anchoring device or is attached at a first end to a second anchoring rod or tube wherein the second anchoring tube fully passes through a hole in an individual attachment anchoring device, and the position or length or the first or second rod that passes partially or fully through the individual anchoring device may be reversibly fixed by a portion of the anchoring device itself or by a set screw located on or within the anchoring device, and wherein at least one end of each adjustable length anchoring tube or rod comprises an attachment point for attaching a tension device, wherein the tension device is attached at its other end to at least one proximal attachment points located on the basic splinting device, (e) a plurality of splinting apparatus for individually splinting each digit whose movement is to be restricted, wherein each individual splinting apparatus has at least one attachment point on a portion of the individual digit splinting apparatus located above the posterior of a digit and attached to one end portion of at least one cord, rope, string or wire and the other end of the cord, rope, string or wire is attached to either an attachment anchoring device located on the outrigger wire or tube or to the end of the first or second anchoring tube or rod.

The present invention relates to one or more of the following features, elements or combinations thereof.

In one embodiment, an apparatus for providing a range of motion to digits on a person's hand is disclosed. The apparatus may include a splint, an outrigger, a plurality of tubes, and a plurality of rubber bands. The outrigger may be secured to the splint and the plurality of tubes may be connected to the outrigger. The plurality of tubes may be provided in varying lengths such that a variety of range of motion requirements may be accommodated by a single kit to implement the apparatus according to the invention.

DETAILED DESCRIPTION OF EMBODIMENTS OF THE INVENTION

Figure 1:
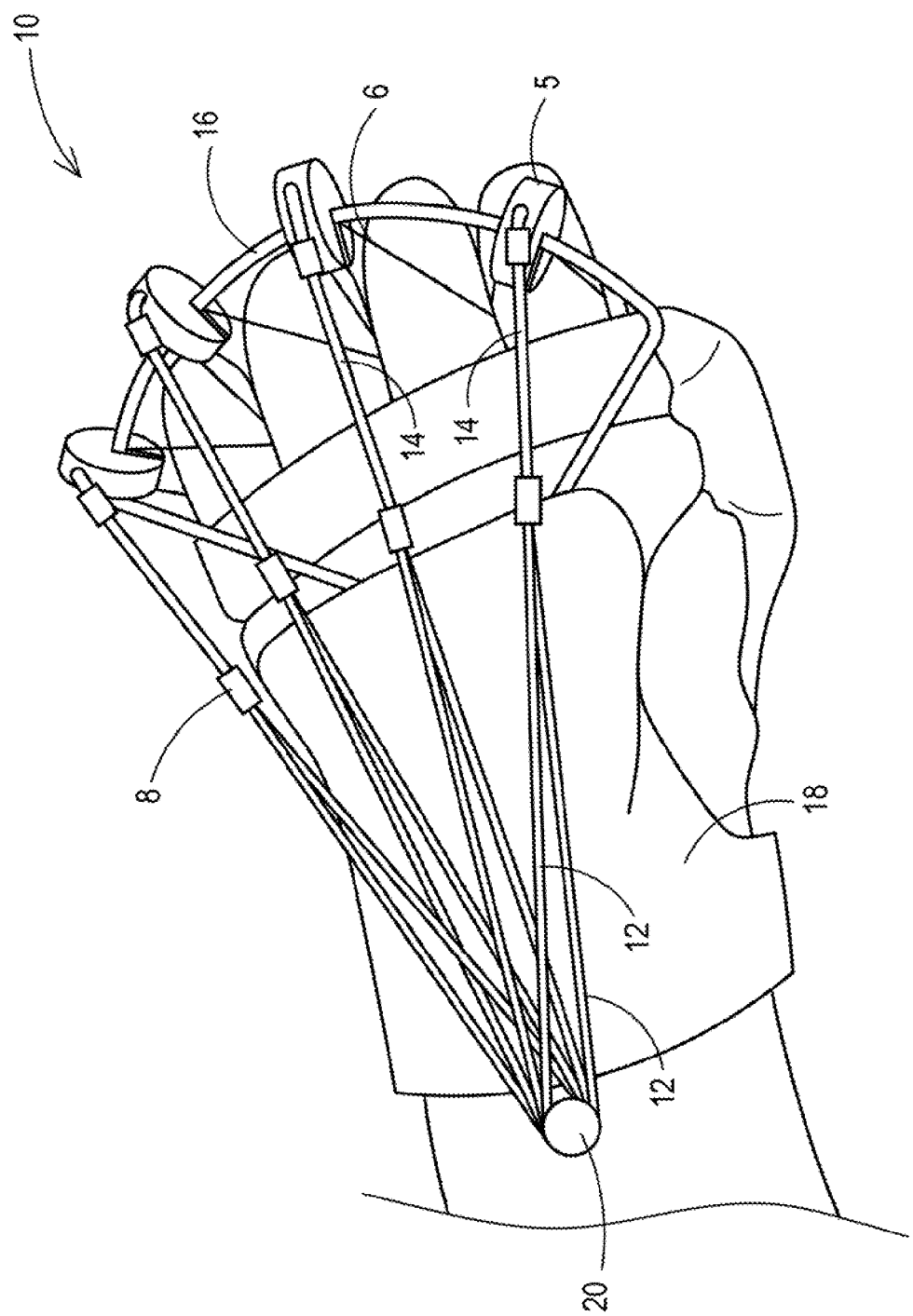
FIG. 1 is a perspective view of one embodiment of the invention having a plurality of single adjustable length anchoring tubes or rods 14.

As can be seen in FIG. 1, one embodiment of the invention comprises a readily adjustable interchangeable range of motion control extremity splinting apparatus 10 comprising a basic splinting device or casting 18 having attached at its distal end attachment points an outrigger wire or tube 16 that slides through a plurality of anchoring devices 5 having attached to each anchoring device 5 a single adjustable length anchoring tube or rod 14 to provide a plurality of adjustable length anchoring tubes or rods 14 to which are attached a plurality of elastomeric tension devices 12 at their portion 8 that are in turn attached to first attachment point 20 located on a proximal portion of the basic splinting device 18 with respect to the persons arm, and a digit movement control cord 6 is attached at one to a extremity digit and at its other end to an anchoring device 5 to collectively provide a plurality of digits movement control cords 6 and a plurality of anchoring devices 5, wherein the length of the plurality of adjustable length anchoring rods 14, the positioning of the plurality of anchoring devices 5, the tension of the plurality of elastomeric tension devices 12 and the length of the plurality of digital movement control cords 6 can be individually adjusted to manage the motion of digits on the splinted extremity (hand) and provide resistance that can aid in rehabilitation, proper range of movement and healing during therapy or during normal activities. In the illustrated example, the motion control extremity splinting apparatus 10 is configured to provide a range of motion from eight centimeters to one and one half centimeters in one half centimeter increments. In the illustrated embodiment, elastomeric tension devices 12 provided are a plurality of rubber bands, wherein the rubber bands being interchangeable and connectable to adjustable length anchoring tubes 14.

According to the present invention, motion control extremity splinting apparatus 10 can create control of motion without slippage. Motion control extremity splinting apparatus 10 can be utilized to treat MP joint arthroplasty, PIP joint arthroplasty, and extensor tendon lacerations, especially in zones 3-5. Also, it may be used with crush injuries and/or fractures with specific range of motion requirements allowed by physicians. Apparatus 10 works well with multi-digit extension and other outrigger kits.

In one embodiment, motion control extremity splinting apparatus 10 comprises a plurality of polymer tubings as adjustable length anchoring rods 14 that are approximately 5 mm wide with lengths of 1.5 cm to 8.0 cm. An outrigger wire 16 is also provided for supporting the adjustable length anchoring rods 14. The adjustable length anchoring rods 14 can illustratively be provided in preset lengths ranging in 5 mm increments to provide for motion adjustment.

Motion control extremity splinting apparatus 10 is designed to support the delivery of safe, timely, and cost effective patient care. This results in more informed and effective treatment, which ultimately leads to improved care and improved patient outcome. Motion control extremity splinting apparatus 10 also works on all dynamic splints saving valuable time and ending frustration.

Figure 2:
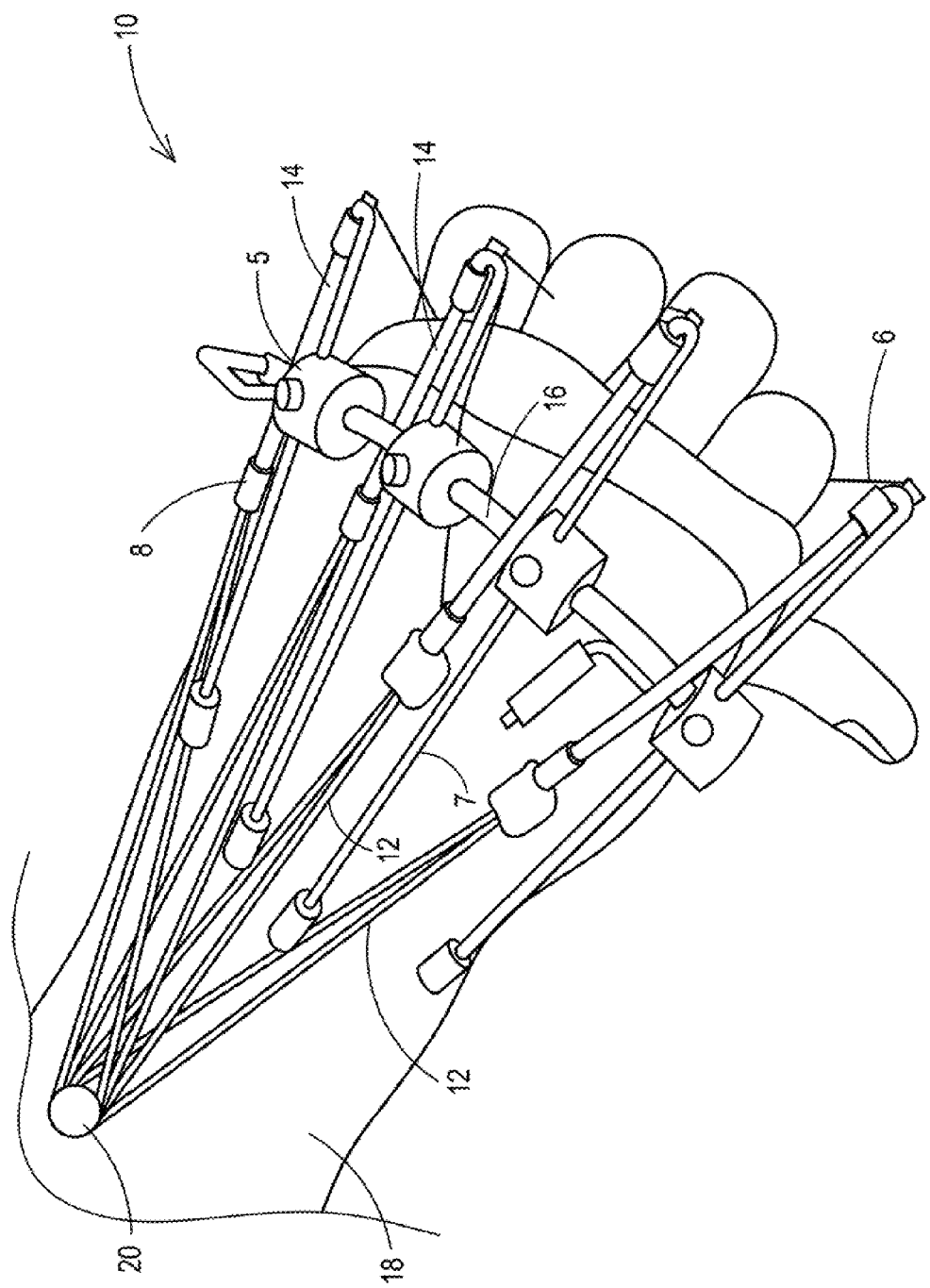
FIG. 2 is a perspective view of another embodiment of the invention having a plurality of paired adjustable length anchoring tubes or rods, pairs of 14 and 7.

In the embodiment shown in FIG. 2, a plurality of paired first adjustable length anchoring tubes or rods 14 and second adjustable length tubes or rods 7 that are connected to one another instead of being connecting to the anchoring devices 5, instead the second adjustable length tubes or rods are passed through a hole in the anchoring devices 5 and anchored by a set screw. This embodiment is referred to as the Rolyan embodiment, wherein a physical therapist can slide the second adjustable length tubes or rods 7 through the anchoring devices 5 and protrude forward beyond the outrigger 16 to provide attachment points for the first adjustable length tubes or rods 14 at their distal end and provide a best starting position for attaching the digital movement control cords 6.

The following steps may be used to implement motion control extremity splinting apparatus 10. A basic splinting device or casting 18 is fabricated and an outrigger 16 is positioned on the distal splint 18 (direction with respect to the arm or leg to which the extremity is attached).

A sling or other type digits splinting apparatus is placed on each or selected fingers that has an anchor on a posterior portion with respect to the hand (back of the hand or fingers, or top of the foot) and a monofilament line 6 is attached to the sling on each digit and then to the distal end of an adjustable length anchoring rod 14. An elastomeric tension device 12 is attached to one end of the adjustable length anchoring rod 14 that has been attached to the monofilament line digital movement control cord 6, and the other end of the elastomeric tension device 12 (rubber band) is secured to a proximal anchoring point 20 on the basic splinting device or casting 18, for example, a rubber band and a hook at proximal anchoring point 20.

A therapist may then assist in flexing (or extending) the digit to the desired degree of movement. At this point, the therapist may place an ink mark on the monofilament line 6 where it touches the distal end of outrigger 16. The digit may then be returned to a neutral position.

While the digit is in a neutral position, the therapist should measure (i.e. in centimeters) the distance between the mark on the monofilament and the end of the stopping point of the outrigger. This measurement determines the appropriate length of adjustable length anchoring rod 14, which may be optionally chosen from a splinting kit according to the invention.

Next, the rubber band may be removed from the end of monofilament line. The monofilament line is then slid through the tubing and the rubber band is replaced at the end of the monofilament and at proximal anchoring point. In such a fashion, the apparatus according to the invention can restrict motion to the point where it will only allow the finger to flex (or extend) the exact amount of degrees set by the therapist and physician.

The tension can be by adding or removing any of the rubber bands 12, modifying the degree of motion adjustments to the other portions of the apparatus, and then reattaching rubber bands to provide tension. This removes any guesswork or re-measuring.

The present invention solves unwanted slippage and movement of various methods and devices used by other therapists worldwide. It alleviates the need for guesswork by patients at home to reset proper degree settings resulting from slippage. Patients without insurance and that cannot afford therapy treatments can now, under doctor's instruction, replace proper degree settings.

In one preferred embodiment, the invention provides a readily adjustable motion control extremity splinting apparatus that is resistant to slipping and does not require frequent replacement of the basic splint when adjustments are required to change the degrees of digit(s) restriction need to be made for physical therapy or for day to day wearing, wherein the splinting apparatus comprises:

(a) a removable or non-removable basic splinting device or casting that is affixed to the limb above an extremity and may be attached to the extremity to restrict movement, comprising one or more distal attachment points with respect to the limb and one or more proximal attachment points with respect to the limb, wherein the proximal and digital attachment points directly or indirectly provide attachment points for adjustable digital movement restriction apparatus, (b) at least one outrigger wire or tube located above and on the posterior portion of the hand and splint, (c) a plurality of attachment anchoring devices having at least two holes, (d) a plurality of single or paired adjustable length anchoring tubes or rods, (e) a plurality of digital splinting apparatus for individually splinting each digit whose movement is to be restricted, each digital splinting apparatus having at least one attachment point for attaching at least one cord, rope, string or wire, wherein the cord, rope or string either attaches to an attachment anchoring device located on the outrigger wire or tube or attached to an end of a single or paired anchoring tube or rod.

A further preferred embodiment of the invention provides a readily adjustable motion control extremity splinting apparatus as described above, wherein the adjustable splinting apparatus comprises:

(a) a removable or non-removable basic splinting device or casting that is affixed to the limb above an extremity and may be attached to the extremity to restrict movement, comprising one or more distal attachment points with respect to the limb and one or more proximal attachment points with respect to the limb, wherein the proximal and digital attachment points directly or indirectly provide attachment points for adjustable digital movement restriction apparatus, (b) an outrigger wire or tube located above and on the posterior portion of the hand and splint wherein the wire or tube is firmly or rotationally attached to one or more distal attachment points of the basic splinting device, as described in (a), and the outrigger wire or tube passes through a hole located in each of a plurality of attachment anchoring devices, (c) a plurality of attachment anchoring devices as described in (b) having at least two perpendicular holes in each anchoring device through which the outrigger tube may be passed and through which a second adjustable length anchoring tube or rod may be passed and may be fixed at a particular length, wherein the attachment anchoring devices may comprise a single unit with at least two perpendicular holes, or may have two portions with matching grooves perpendicular to a single hole wherein the matching groves collectively form a round hole when the two portions are affixed together around the outrigger wire or tube, and optionally comprising a further hole or outlet as an attachment point for a cord, rope, string or wire, (d) a plurality of adjustable length anchoring tubes or rods, wherein a portion of each anchoring tube or rod partially or fully passes through a hole in an individual attachment anchoring device or is attached at a first end to a second anchoring rod or tube wherein the second anchoring tube fully passes through a hole in an individual attachment anchoring device, and the position or length or the first or second rod that passes partially or fully through the individual anchoring device may be reversibly fixed by a portion of the anchoring device itself or by a set screw located on or within the anchoring device, and wherein at least one end of each adjustable length anchoring tube or rod comprises an attachment point for attaching a tension device, wherein the tension device is attached at its other end to at least one proximal attachment points located on the basic splinting device, (e) a plurality of splinting apparatus for individually splinting each digit whose movement is to be restricted, wherein each individual splinting apparatus has at least one attachment point on a portion of the individual digit splinting apparatus located above the posterior of a digit and attached to one end portion of at least one cord, rope, string or wire and the other end of the cord, rope, string or wire is attached to either an attachment anchoring device located on the outrigger wire or tube or to the end of the first or second anchoring tube or rod.

Another preferred embodiment of the invention provides a kit comprising basic splinting apparatus, rubber bands of varying lengths and thicknesses, particular sizes of finger splint or toe splint anchors, various lengths of a plurality of both anchoring rods or anchoring rod pairs, outrigger wiring or tubing and a plurality of anchoring devices that the outrigger wiring or tubing can pass through, monofilament and splint attachment points anchoring devices that can be imbedded in the basic splinting apparatus or affixed thereon.

Figure 3:
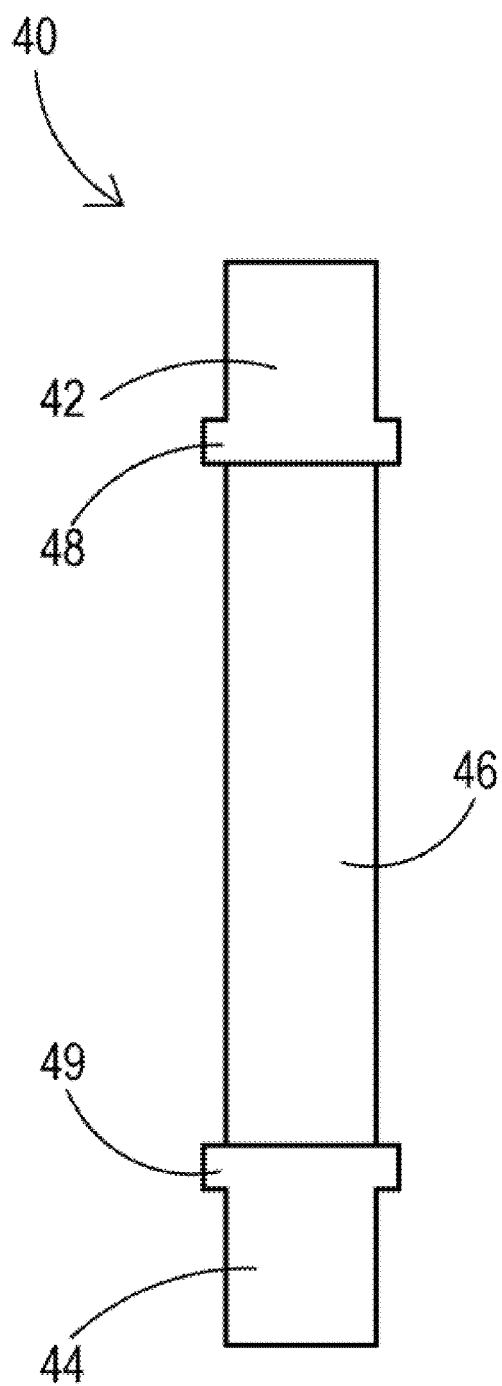
FIG. 3 is a drawing of another embodiment of the present invention.

In FIG. 3, as in one embodiment shown is a rod 40. Rod 40 may be adjustable length anchoring rod 14. The rod 40 has a first end 42 and a second end 44 with a cylinder 46 connecting the first end 42 and a second end 44. The first end 42 and the second end 44 oppose each other. The first end 42 has a first end shoulder 48 and the second end 44 has a second end shoulder 49.

Figure 4:
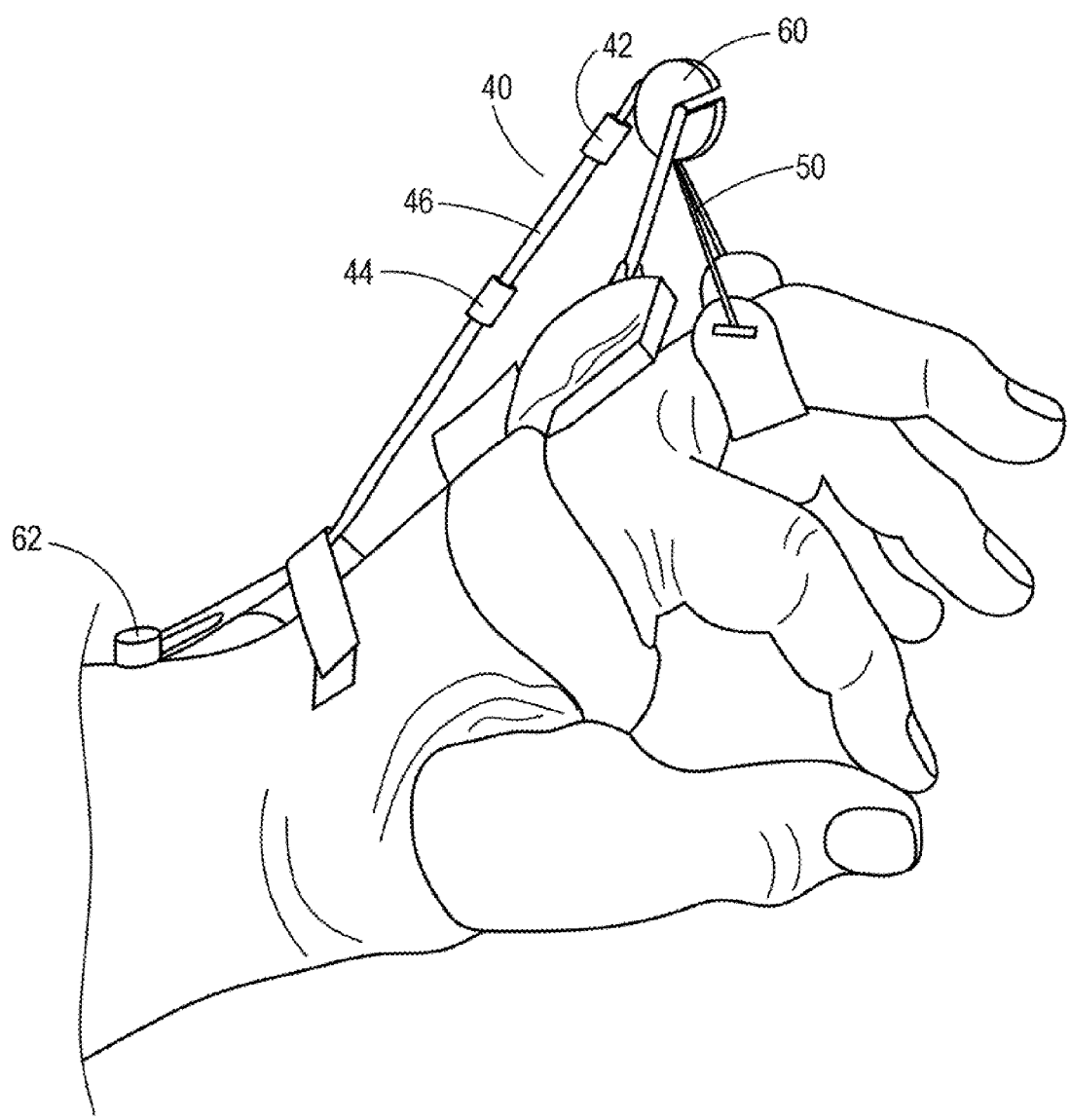
FIG. 4 is a drawing of another embodiment of the present invention.

In FIG. 4 as in one embodiment shown is the rod 40 with the first end 42 and the second end 44 with the cylinder 46 allowing a finger cord 50 to pass through the inside of the cylinder 46. This allows the finger cord 50 to support each finger on one end and be anchored to the user's wrist area on the other end of the finger cord 50. The rod 40 allows finger cord 50 to connect to a pulley 60 at the first end 42, the rod 40 is connected to a rubber band post 62 on the second end 44. The arrangement of the rod 40 between the pulley 60 and the rubber band post 62 allows a health care provider to select a specific range of motion needed for proper hand therapy. This range of motion will change with a patient's needs for example after hand surgery and while healing the range of motion desired will change. The rod 40 is easily changed and available in different lengths to provide a health car provider the desired range of motion.

While the disclosure is susceptible to various modifications and alternative forms, specific exemplary embodiments thereof have been shown by way of example in the drawings and have herein been described in detail. It should be understood, however, that there is not intent to limit the disclosure to the particular embodiments disclosed, but on the contrary, the intention is to cover all modifications, equivalents, and alternatives falling within the spirit and scope of the disclosure as defined by the appended claims.

What is claimed is:

1. A readily adjustable motion control extremity splinting apparatus that is resistant to slipping, comprises:
(a) a splinting device or casting that is affixed to a limb to restrict movement, wherein the device or casting includes one or more distal attachment points and one or more rubber band posts, wherein the rubber band posts and distal attachment points provide adjustable digital movement;
(b) at least one outrigger wire or tube located above and on a posterior portion of the splinting device, wherein the wires or tubes are firmly or rotationally attached to one or more distal attachment points of the basic splinting device and the outrigger wire or tube passes through a hole located in each of the plurality of attachment anchoring devices;
(c) a plurality of attachment anchoring devices that include a plurality of pulleys having at least two perpendicular holes disposed on each anchoring device through which the outrigger tube is passed and through which a second adjustable length anchoring tube or rod is passed and is fixed at a particular length, wherein the attachment anchoring devices include a single unit with at least two perpendicular holes or two portions with matching grooves perpendicular to a single hole wherein the matching groves collectively form a round hole when the two portions are affixed together around the outrigger wire or tube;
(d) a plurality of single or paired adjustable length anchoring tubes or rods wherein a portion of the anchoring tubes or rods partially or fully passes through a hole in the individual attachment anchoring device or is attached at a first end of a second anchoring rod or tube wherein the second anchoring tube fully passes through a hole in the individual attachment anchoring device and the position or length or the first or second rod that passes partially or fully through the individual anchoring device that is reversibly fixed by the anchoring device or by a set screw located on or within the anchoring device, wherein at least one end of each of the adjustable length anchoring tube or rod includes an attachment point to attach a tension device, wherein the tension device is attached to the at least one rubber band posts located on the splinting device;
(e) a plurality of digital splinting apparatuses to individually splint each of the digits whose movement is restricted, wherein each of the splinting apparatus has at least one attachment point on a portion of the individual digit splinting apparatus located above the posterior of the digits and is attached to one end portion of at least one cord, rope, string or wire and another end portion of the cord, the rope, the string or the wire attached to the attachment anchoring device located on the outrigger wire or tube or to the end of the first or second anchoring tube or rod.

2. The motion control extremity splinting apparatus according to claim 1, wherein the adjustable length tubing or anchoring rods are approximately 5 mm in diameter and in the range of approximately 1.5 cm to 8.0 cm in length and have flexibility to avoid injury.

3. The motion control extremity splinting apparatus according to claim 1, wherein the single adjustable length tubing or anchoring rods are attached to each of the digits.

4. The motion control extremity splinting apparatus according to claim 1, wherein the motion control extremity splinting apparatus includes a pair of adjustable length tubing or anchoring rods attached to each digit and the pair of adjustable length tubing or anchoring rods are removably attached to one another.

5. The motion control extremity splinting apparatus according to claim 1, wherein the adjustable length tubing or anchoring rods are made of a hard plastic or aluminum tubing.

6. A method for providing a readily adjustable motion control extremity splinting apparatus, comprising the steps of:
a) fabricating a basic splinting device or casting,
b) positioning an outrigger wire or tube on a distal end of the splinting apparatus on an arm or a leg that is being splinted, wherein the outrigger wire or tube is first passed through a plurality of anchoring devices prior to being positioned on the distal end of the splinting apparatus;
c) attaching a sling or other type of digits splinting apparatus on each or a selected plurality of fingers, wherein the apparatus has an anchor on a posterior portion attached to a back of a hand or a top of a foot;
d) attaching a cord, a rope, a wire or a string to each of the slings on each of the digits and attaching an end of the cord, the rope, the wire or the string to a distal end of an adjustable length anchoring rod that is anchored to an anchoring device located on the outrigger wire or tubing;
e) attaching a first end of a plurality of elastomeric tension devices to one end of the plurality of the adjustable length anchoring rods that have been attached to the cord, the rope, the wire or the string and attaching a second end of a plurality of elastomeric tension devices to one or more anchors at a proximal anchoring point on the basic splinting device or casting.

7. The method according to claim 6, wherein the method further comprises;
i) flexing or extending the digit to a desired degree of movement;
ii) placing a mark or other indication on a wire, a rope, a string, or a cord attached to a sling on the digit where it touches the distal end of the outrigger at said desired degree of movement;
iii) returning the digit to a neutral position;
iv) measuring a distance between the mark or other indicator and the end of a stopping point of the outrigger to determine an appropriate length of the adjustable length anchoring rod; and
v) removing tension to said digit to make adjustments to said apparatus and then replacing tension to said digit.

8. The method according to claim 6, wherein a pair of the adjustable length tubing or anchoring rods attached to each digit are used and each pair of adjustable length tubing or anchoring rods are removably attached.

9. A kit to construct an apparatus, comprising:
a basic splinting apparatus;
a plurality of rubber bands of a plurality of varying lengths and thicknesses;
a plurality of finger splints or toe splint anchors;
a plurality of both anchoring rods or anchoring rod pairs, outrigger wiring or tubing; and
a plurality of anchoring devices that the outrigger wiring or tubing can pass through, with a plurality of monofilament cords and splint attachment points anchoring devices that can be imbedded in the basic splinting apparatus or affixed thereon.

10. The kit according to claim 9, further comprising:
an outrigger configured to be mounted on a splint,
a plurality of tubes, each of the tubes defining a length,
a plurality of slings, and
a plurality of rubber bands, wherein the plurality of tubes include the tubes of varying lengths.

11. The kit according to claim 10, wherein said kit includes a plurality of prefabricated and fabricated basic splint or splint portions.

12. The kit according to claim 9, wherein the kit is utilized on a person's hand and the outrigger is configured to be positioned distally outwardly from the knuckles of the hand.

13. The kit according to claim 12, wherein the plurality of tubes are manufactured from polymer tubing about 5 mm in diameter and the monofilament line and splints or slings with anchoring points of a size to fit around a plurality of fingers on said person's hand.

14. The kit according to claim 13, wherein the plurality of tubes are provided in a plurality of sets of 5 mm increments in length in a range from about 1.5 cm to 8.0 cm in length.

* * * * *